(12) United States Patent
Corma et al.

(10) Patent No.: US 7,166,751 B2
(45) Date of Patent: Jan. 23, 2007

(54) METHOD FOR MANUFACTURING CYCLOALKANOL AND/OR CYCLOALKANONE

(75) Inventors: Avelino Corma, Valencia (ES); Jose Manuel Lopez Nieto, Paterna (ES)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 11/390,160

(22) Filed: Mar. 28, 2006

(65) Prior Publication Data

US 2006/0224020 A1 Oct. 5, 2006

(30) Foreign Application Priority Data

Mar. 30, 2005 (JP) .......................... P2005-097488

(51) Int. Cl.
*C07C 454/00* (2006.01)
(52) U.S. Cl. ....................... 568/357; 568/344; 568/431
(58) Field of Classification Search ................ 568/344, 568/357, 431
See application file for complete search history.

(56) References Cited

U.S. PATENT DOCUMENTS 6,160,183 A 12/2000 Druliner et al.

OTHER PUBLICATIONS

Rui Zhao, et al., "A highly efficient oxidation of cyclohexane over Au/ZSM-5 molecular sieve catalyst with oxygen as oxidant", Chemical Communications (United Kingdom) 2004, pp. 904-905.
G. Lu[a], et al. "Gold nanoparticles in mesoporous materials showing catalytic selective oxidation cyclohexane using oxygen", Applied Catalysis A: General (the Netherlands) 280, 2005, pp. 175-180.
S. Velu et al., "Vapor phase hydrogenation of phenol over palladium supported on mesoporous $CeO_2$ and $ZrO_2$", Applied Catalysis A: General, vol. 245, No. 2, (2003), pp. 317-331.
T. Takeguchi et al, "Determination of dispersion of precious metals on $CeO_2$—containing supports", Applied Catalysis, A: General, vol. 293, (2005), pp. 91-96.

*Primary Examiner*—J. Parsa
(74) *Attorney, Agent, or Firm*—Sughrue Mion, PLLC

(57) ABSTRACT

The object of the present invention is to provide a method for manufacturing cycloalkanol and/or cycloalkanone with favorable selectivity coefficient by oxidizing cycloalkane with favorable degree of conversion.

In the present invention, cycloalkane is oxidized with oxygen in the presence of a catalyst such that gold is supported on ceric oxide. Said oxidation is preferably performed in the presence of a free-radical initiator and the free-radical initiator is preferably 2,2'-azobis(isobutyronitrile).

5 Claims, No Drawings

METHOD FOR MANUFACTURING CYCLOALKANOL AND/OR CYCLOALKANONE

CROSS-REFERENCE TO RELATED APPLICATIONS

The present application claims priority under U.S.C. § 119 to Japanese Patent Application No. 2005-097488 (filed on Mar. 30, 2005, entitled "Method for Manufacturing Cycloalkanol and/or Cycloalkanone"). The contents of that application are incorporated herein by reference thereto in their entirety.

BACKGROUND OF THE INVENTION

1. Technical Field

The present invention relates to a method for manufacturing cycloalkanol and/or cycloalkanone by oxidizing cycloalkane with oxygen.

2. Description of the Related Art

A method of using a gold-supporting catalyst is proposed as one of methods for manufacturing cycloalkanol and/or cycloalkanone by oxidizing cycloalkane with oxygen. For example, the above-mentioned oxidation by using a catalyst such that gold is supported on silica, alumina, zirconia, carbon or titania is disclosed in U.S. Pat. No. 6,160,183. Also, the above-mentioned oxidation by using a catalyst such that gold is supported on zeolite ZSM-5 is disclosed on pp. 904 to 905 of Chemical Communications (the United Kingdom), 2004. Further, the above-mentioned oxidation by using a catalyst such that gold is supported on mesoporous substance MCM-41 or SBA-15 is disclosed on pp. 175 to 180 of Applied Catalysis A: General (the Netherlands), 2005.

SUMMARY OF THE INVENTION

The above-mentioned conventional methods include unsatisfactory points in view of activity and selectivity of a catalyst, namely, degree of conversion of cycloalkane and selectivity coefficient of cycloalkanol and/or cycloalkanone. The object of the present invention is to provide a method of capably manufacturing cycloalkanol and/or cycloalkanone with favorable selectivity coefficient by oxidizing cycloalkane with favorable degree of conversion through oxidation of cycloalkane with the use of a gold-supporting catalyst.

Through earnest studies, the inventors of the present invention have completed the present invention by finding out that the adoption of ceric oxide as a carrier of a gold-supporting catalyst allows the above-mentioned object to be achieved. That is to say, the present invention provides a method for manufacturing cycloalkanol and/or cycloalkanone by oxidizing cycloalkane with oxygen in the presence of a catalyst such that gold is supported on ceric oxide.

The present invention allows cycloalkanol and/or cycloalkanone to be manufactured with favorable selectivity coefficient by oxidizing cycloalkane with favorable degree of conversion.

DETAILED DESCRIPTION OF THE INVENTION

The present invention is hereinafter detailed. In the present invention, corresponding cycloalkanol and/or cycloalkanone are manufactured by using cycloalkane for raw materials to oxidize this with oxygen (molecular oxygen) in the presence of a catalyst.

Examples of cycloalkane for raw materials include, for example, monocyclic cycloalkane having no substituent in a ring such as cyclopropane, cyclobutane, cyclopentane, cyclohexane, cycloheptane, cyclooctane, cyclodecane and cyclooctadecane, polycyclic cycloalkane such as decalin and adamantane, and cycloalkane having substituent in a ring such as methylcyclopentane and methylcyclohexane, and also two kinds or more thereof can be used as required.

Oxygen-containing gas is typically used for oxygen source. This oxygen-containing gas may be, for example, air, pure oxygen, or air or pure oxygen diluted with inert gas such as nitrogen, argon and helium. Oxygen enriched air in which pure oxygen is added to air can also be used.

With regard to the present invention, gold supported on ceric oxide (hereinafter occasionally referred to as 'gold-supporting ceric oxide') is used as a catalyst for oxidizing cycloalkane with oxygen. The use of such a catalyst allows cycloalkanol and/or cycloalkanone to be manufactured with favorable selectivity coefficient by oxidizing cycloalkane with favorable degree of conversion.

An oxide of cerium with an oxidation number of 4, namely, ceria is typically used for ceric oxide as a carrier. The support percentage of gold is typically 0.1 to 20% in weight percentage with respect to a catalyst, namely, gold-supporting ceric oxide, preferably 0.5 to 10%. The specific surface area of this gold-supporting ceric oxide is preferably approximately 50 to 300 $m^2/g$ and the average particle diameter of supported gold is preferably 10 nm or less.

Examples of a method for supporting gold on ceric oxide include, for example, a method such as to impregnate ceric oxide with an aqueous solution of gold compounds such as halogen acid of gold and salts thereof, a method such as to immerse ceric oxide in an aqueous solution of gold compounds and adsorb gold compounds with ceric oxide and the like.

The oxidation reaction of cycloalkane can be performed by contacting cycloalkane with oxygen in the presence of gold-supporting ceric oxide as a catalyst. The used quantity of a catalyst is typically 0.01 to 50 parts by weight with respect to 100 parts by weight of cycloalkane, preferably 0.1 to 10 parts by weight.

The coexistence of a free-radical initiator is advantageous to an improvement in degree of conversion of cycloalkane. Examples of a free-radical initiator include a zonitrile compounds such as 2,2'-azobis(isobutyronitrile), 2,2'-azobis(2,4-dimethylvaleronitrile) and 2,2'-azobis(4-methoxy-2,4-dimethylvaleronitrile), and peroxides such as peroxydibenzoyl, peroxydilauroyl, tert-butylperoxy 2-ethylhexanoate and bis (2-ethylhexyl)peroxydicarbonate, and also two kinds or more thereof may be used together as required. Among them, azonitrile compounds are preferable, particularly preferably 2,2'-azobis(isobutyronitrile). The used quantity of a free-radical initiator is typically 0.1 mol time or less with respect to cycloalkane.

The reaction temperature is typically 0 to 200° C., preferably 50 to 170° C. and the reaction pressure is typically 0.01 to 10 MPa, preferably 0.1 to 2 MPa. The reaction solvent can be used as required, for example including nitrile solvents such as acetonitrile and benzonitrile, and carboxylic acid solvents such as acetic acid and propionic acid.

The after-treatment after oxidation reaction is not particularly limited, for example including a process such as to filter the reaction mixture to separate a catalyst therefrom, which mixture is thereafter washed by water and subsequently distilled. In the case where cycloalkylhydroperoxide corresponding to cycloalkane for raw materials is contained in the reaction mixture, cycloalkylhydroperoxide can be converted into intended cycloalkanol and cycloalkanone by alkali treatment, reduction treatment and the like.

EXAMPLES

Examples of the present invention are hereinafter described and the present invention is not limited thereto. The analysis of cyclohexane, cyclohexanone and cyclohexanol in reaction liquid was performed by gas chromatography, and degree of conversion of cyclohexane as well as each selectivity coefficient of cyclohexanone and cyclohexanol were calculated from results of this analysis.

Reference Example 1 (preparation of gold-supporting ceric oxide)

0.6 g (1.5 mmol) of tetrachloroauric (III) acid·trihydrate was dissolved in 70 ml of water to obtain an aqueous solution, which was subsequently adjusted to pH 10 by 0.2 M sodium hydroxide aqueous solution. Meanwhile, 5.7 g (33 mmol) of ceric oxide and 200 ml of water were mixed and stirred at room temperature, and the above-mentioned aqueous solution was added to this suspension and stirred at room temperature for 15 hours. The obtained solid was filtered out and washed in water, and thereafter dried at a temperature of 100° C. for a whole day and night to obtain gold-supporting ceric oxide. The support percentage of gold in this gold-supporting ceric oxide was 4.5 weight % as a result of ultimate analysis. The specific surface area of the gold-supporting ceric oxide was 145 $m^2/g$ as a result of analysis by BET method, and the average particle diameter of gold was 4 nm or less as a result of X-ray diffraction (XRD) analysis.

Reference Example 2 (preparation of gold-supporting MCM-41)

1.2 g (3.0 mmol) of tetrachloroauric (III) acid·trihydrate was dissolved in 100 ml of water to obtain an aqueous solution, which was subsequently adjusted to pH 10 by 0.2 M sodium hydroxide aqueous solution. Meanwhile, 6.0 g of MCM-41 (a specific surface area of 1000 $m^2/g$ by BET method) and 200 ml of water were mixed and stirred at room temperature, and the above-mentioned aqueous solution was added to this suspension and stirred at room temperature for 15 hours. The obtained solid was filtered out and washed in water, and thereafter dried at a temperature of 100° C. for 12 hours to obtain gold-supporting MCM-41 such that gold is supported on MCM-41. The support percentage of gold in this gold-supporting MCM-41 was 4.5 weight % as a result of ultimate analysis.

Example 1

2.5 g (30 mmol) of cyclohexane and 0.10 g of gold-supporting ceric oxide obtained in Reference Example 1 as a catalyst were put in a 12-ml autoclave, and the inside of the system was pressurized up to 1.5 MPa with oxygen at room temperature and thereafter heated up to a temperature of 120° C. and reacted for 24 hours. As a result of analyzing the reaction liquid, degree of conversion of cyclohexane was 2.0%, selectivity coefficient of cyclohexanone was 25.3% and selectivity coefficient of cyclohexanol was 35.9%.

Example 2

2.5 g (30 mmol) of cyclohexane and 0.10 g of gold-supporting ceric oxide obtained in Reference Example 1 as a catalyst were put in a 12-ml autoclave, to which 0.075 g (0.46 mmol) of 2,2'-azobis(isobutyronitrile) was further added as a free-radical initiator, and the inside of the system was pressurized up to 1.5 MPa with oxygen at room temperature and thereafter heated up to a temperature of 120° C. and reacted for 24 hours. As a result of analyzing the reaction liquid, degree of conversion of cyclohexane was 20.8%, selectivity coefficient of cyclohexanone was 37.8% and selectivity coefficient of cyclohexanol was 52.5%.

Example 3

The reaction was performed in the same manner as Example 2 except for pressurizing the inside of the system by using air instead of oxygen. As a result of analyzing the reaction liquid, degree of conversion of cyclohexane was 14.0%, selectivity coefficient of cyclohexanone was 28.5% and selectivity coefficient of cyclohexanol was 64.8%.

Comparative Example 1

The reaction was performed in the same manner as Example 1 except for replacing gold-supporting ceric oxide obtained in Reference Example 1 with gold-supporting MCM-41 obtained in Reference Example 2 as a catalyst. As a result of analyzing the reaction liquid, degree of conversion of cyclohexane was 1.7%, selectivity coefficient of cyclohexanone was 16.6% and selectivity coefficient of cyclohexanol was 28.5%.

Comparative Example 2

The reaction was performed in the same manner as Example 2 except for replacing gold-supporting ceric oxide obtained in Reference Example 1 with gold-supporting MCM-41 obtained in Reference Example 2 as a catalyst. As a result of analyzing the reaction liquid, degree of conversion of cyclohexane was 10.5%, selectivity coefficient of cyclohexanone was 31.3% and selectivity coefficient of cyclohexanol was 48.5%.

The major embodiments and the preferred embodiments of the present invention are listed below.

[1] A method of manufacturing cycloalkanol and/or cycloalkanone wherein cycloalkane is oxidized with oxygen in the presence of a catalyst such that gold is supported on ceric oxide.

[2] The method according to [1], wherein said oxidation is performed in the presence of a free-radical initiator.

[3] The method according to [2], wherein the free-radical initiator is an azonitrile compound.

[4] The method according to [2], wherein the free-radical initiator is 2,2'-azobis(isobutyronitrile).

[5] The method according to any one of [1] to [4], wherein the cycloalkane is cyclohexane.

What is claimed is:

1. A method for manufacturing cycloalkanol and/or cycloalkanone wherein cycloalkane is oxidized with oxygen in the presence of a catalyst such that gold is supported on ceric oxide.

2. The method according to claim 1, wherein said oxidation is performed in the presence of a free-radical initiator.

3. The method according to claim 2, wherein the free-radical initiator is an azonitrile compound.

4. The method according to claim 2, wherein the free-radical initiator is 2,2'-azobis(isobutyronitrile).

5. A method according to any one of claims 1 to 4, wherein the cycloalkane is cyclohexane.

* * * * *